United States Patent
Sinha et al.

(10) Patent No.: US 8,941,398 B2
(45) Date of Patent: *Jan. 27, 2015

(54) HEAT SPREADER FLATNESS DETECTION

(71) Applicant: International Business Machines Corporation, Armonk, NY (US)

(72) Inventors: Arvind K. Sinha, Rochester, MN (US); Kory W. Weckman, Fargo, ND (US)

(73) Assignee: International Business Machines Corporation, Armonk, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/964,167

(22) Filed: Aug. 12, 2013

(65) Prior Publication Data

US 2013/0321008 A1  Dec. 5, 2013

Related U.S. Application Data

(63) Continuation of application No. 13/033,637, filed on Feb. 24, 2011, now Pat. No. 8,558,564.

(51) Int. Cl.
*G01R 27/08* (2006.01)
*G01R 31/08* (2006.01)
*G01N 27/04* (2006.01)
*H05K 7/20* (2006.01)

(52) U.S. Cl.
CPC .......... *G01N 27/041* (2013.01); *H05K 7/20509* (2013.01)
USPC .......................................... 324/697; 324/525

(58) Field of Classification Search
USPC ......... 324/697, 693, 691, 649, 600, 549, 525, 324/512, 500; 257/717, 718, 719, 720, 706, 257/625, E33.075, E31.131, E23.051, 257/E23.08, E23.101

See application file for complete search history.

(56) References Cited

U.S. PATENT DOCUMENTS

| 5,574,668 | A  | 11/1996 | Beaty           |
|-----------|----|---------|-----------------|
| 5,877,088 | A  | 3/1999  | Samitsu et al.  |
| 6,653,702 | B2 | 11/2003 | Ishio et al.    |
| 7,102,226 | B2 | 9/2006  | Fitzgerald et al.|
| 7,182,668 | B2 | 2/2007  | Marshall        |
| 7,473,030 | B2 | 1/2009  | Bruce et al.    |
| 7,500,460 | B2 | 3/2009  | Mukouhara       |
| 7,559,247 | B2 | 7/2009  | Otsuka et al.   |

(Continued)

FOREIGN PATENT DOCUMENTS

JP    2003023039    1/2003

OTHER PUBLICATIONS

IBM Technical Disclosure, "Intelligent Multi-Chip-Module (MCM) Package Enhancement," IPCOM000035293D, Jan. 20, 2005, www.ip.com.

(Continued)

*Primary Examiner* — Hoai-An D Nguyen
(74) *Attorney, Agent, or Firm* — Matthew C. Zehrer

(57) ABSTRACT

A heat spreader includes a plurality of sensors that indicate that the heat spreader is flat against a chip stack. One or more nodes within a sensor are electrically connected. The electrical resistance values of the connection may be compared to determine if the nodes within the sensors are relatively flat. Sensor flatness may be correlated to heat spreader flatness for determining whether the heat spreader is flat against the chip stack when the heat spreader is installed upon the chip stack.

20 Claims, 5 Drawing Sheets

(56) References Cited

U.S. PATENT DOCUMENTS 8,081,474 B1 12/2011 Zohni et al.
8,558,564 B2 * 10/2013 Sinha et al. .................. 324/697

OTHER PUBLICATIONS

"Intel Strain Measurement Methodology for Circuit Board Assembly—Board Flexure Initiative (BFI)", Intel Manufacturing Enabling Guide, May 2010.

Bo Song, "Reliability Evaluation of Stacked Die BGA Assemblies Under Mechanical Bending Loads," 2006.

R. Tummala et al., "Japan's Electronic Packaging Technologies," JETC Panel on Electronic Manufacturing and Packaging in Japan, Final Report, Feb. 1995, http://www.wtec.org/lovola/text/elecpack/10_ch4.txt.

K. Kanbach et al., "3D Si-on-Si stack packaging," Soldering & Surface Mount Technology, vol. 12, Iss 1, pp. 35-39, 2000, Abstract, http://www.emarldinsight.com/journals.htm?articleid=1508852.

* cited by examiner

HEAT SPREADER FLATNESS DETECTION

FIELD OF THE INVENTION

The present invention generally relates to cooling heat generating components in electronic systems and to detecting if a heat spreader is loaded flat against and in thermal contact with the heat generating components.

SUMMARY OF THE INVENTION

An apparatus, method, and computer program product embodiments generally relate to a heat spreader that includes at least one sensor that indicates that the heat spreader is flat against a chip stack. In certain embodiments, one or more nodes within a sensor are electrically connected. In another embodiment, the connection resistances may be compared to determine if the nodes within the sensor is relatively flat. The sensor flatness may be correlated to heat spreader flatness against the chip stack upon installation of the heat spreader to the chip stack. In other embodiments, sensor flatness may be communicated to a higher level electronic device such as a visual display that may be viewed by a user to determine whether the heat spreader is flat against the chip stack.

These and other embodiments, features, aspects, and advantages will become better understood with reference to the following description, appended claims, and accompanying Figs.

BRIEF DESCRIPTION OF THE DRAWINGS

So that the manner in which the above recited features of the present invention are attained and can be understood in detail, a more particular description of the invention, briefly summarized above, may be had by reference to the embodiments thereof which are illustrated in the appended figures.

It is to be noted, however, that the appended figures illustrate only typical embodiments of this invention and are therefore not to be considered limiting of its scope.

DETAILED DESCRIPTION OF THE PREFERRED EMBODIMENTS

Figure 1:
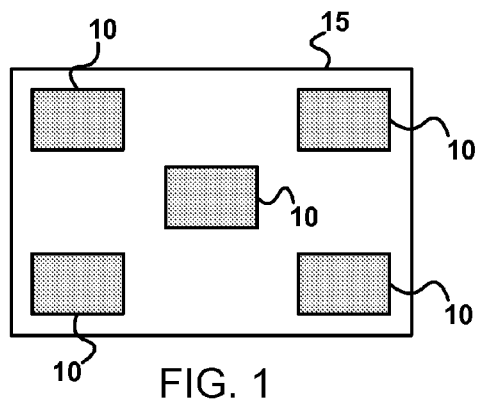
FIG. 1 depicts a heat spreader according to an embodiment of the present invention.

It will be readily understood that the components of the present invention, as generally described and illustrated in the Figs. herein, may be arranged and designed in a wide variety of different configurations. Thus, the following detailed description of the embodiments of the apparatus, device, method, or computer program product of the present invention, as represented in FIGS. 1 through 15, is not intended to limit the scope of the invention, as claimed, but is merely representative of selected embodiments of the invention.

As will be appreciated by one skilled in the art, various embodiments of the present invention may be embodied as a device, method, computer program product or any combination thereof. Accordingly, embodiments of the present invention may take the form of an entirely hardware embodiment, an entirely software embodiment (including firmware, resident software, micro-code, etc.) or an embodiment combining software and hardware aspects that may all generally be referred to, for example as a "system." Furthermore, embodiments of the present invention may take the form of a computer program product embodied in a tangible medium of expression having computer usable program code embodied thereupon.

Any combination of one or more tangible computer usable or computer readable medium(s) may be utilized. The computer-usable or computer-readable medium may be, for example but not limited to, an electronic, magnetic, optical, electromagnetic, infrared, or semiconductor system, apparatus, device, or propagation medium. More specific examples (a non-exhaustive list) of the computer-readable medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CDROM), an optical storage device, a tangible transmission media such as those supporting the Internet or an intranet, or a magnetic storage device. In the context of this document, a computer-usable or computer-readable medium may be any tangible medium that can contain, store, communicate, propagate, or transport the program for use by or in connection with the instruction execution system, apparatus, or device.

Computer program code for carrying out operations of embodiments of the present invention may be written in any combination of one or more programming languages, including an object oriented programming language such as Java, Smalltalk, C++ or the like and conventional procedural programming languages, such as the "C" programming language or similar programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Reference throughout this specification to "one embodiment" or "an embodiment" (or the like) means that a particular feature, structure, or characteristic described in connection with the embodiment is included in at least one embodiment of the present invention. Thus, appearances of the phrases "in one embodiment" or "in an embodiment" in various places throughout this specification are not necessarily all referring to the same embodiment. In addition, features described in connection with a particular embodiment may be combined or excluded from other embodiments described herein.

Certain embodiments of the present invention are described below with reference to flowchart illustrations or block diagrams of methods. It will be understood that each block of the flowchart illustrations or block diagrams of methods can be implemented by computer program instructions. These computer program instructions may be provided to a processor of a general purpose computer, special purpose computer, or other programmable data processing apparatus to produce a particular apparatus, such that the instructions, which execute via the processor of the computer or other programmable data processing apparatus, create means for implementing the functions/acts specified in the flowchart or block diagram block or blocks.

An exemplary computer processing system adapted to implement one or more method embodiments of the present invention may comprise: a processor which may comprise a digital signal processor, central processing unit, microcontroller, microprocessor, microcomputer, ASIC or FPGA core. The computer processing system may also comprise static read only memory and dynamic main memory all in communication with the processor. The processor is also in communication, for example via a bus, with a number of peripheral devices that are also included in the computer system. Peripheral devices coupled to the bus may include for example a display device (e.g., monitor), alpha-numeric input device (e.g., keyboard) and pointing device (e.g., mouse, tablet, etc.)

The computer processing system may be connected to one or more external networks such as a LAN or WAN via communication lines connected to the system via data I/O communications interface (e.g., network interface card, wireless network interface card, etc.). The network adapters coupled to the computer processing system enable the computer processing system to become coupled to other data processing systems or remote printers or storage devices through intervening private or public networks. Modems, cable modem and Ethernet cards are just a few of the currently available types of network adapters. The system may also comprise magnetic, semiconductor based, or other such storage device(s) for storing application programs and data. The computer processing system may also comprise a tangible computer readable storage medium.

The depictions in the Figs. illustrate the architecture, functionality, or operation of possible implementations of systems, devices, methods or computer program products according to various embodiments of the present invention. In this regard, the flowchart illustrations or block diagrams of methods may represent a module, segment, or portion of code, which comprises one or more executable instructions for implementing the specified logical function(s). The functions noted in the block may occur out of the order noted in the Figs. For example, two blocks shown in succession may, in fact, be executed substantially concurrently, or the blocks may sometimes be executed in the reverse order, depending upon the functionality involved. And unless otherwise understood in the art, each functional block in the apparatus, device, or system Figs. may represent one or more discrete or indiscrete components. For example a block in the apparatus, device, or system Figs. could be implemented by special purpose hardware-based or hardware/software based system that performs the specified functions or acts as described herein.

FIG. 1 depicts a bottom view of a heat spreader 15 according to various embodiments of the present invention. Heat spreader 15 moves or otherwise transfers heat from a heat source. In certain embodiments, heat spreader 15 cools one or more heat generating electronic components within an electronic system. Heat spreader 15 may be for example a copper plate. Alternatively, heat spreader 15 may be made from another material that has a relatively high thermal conductivity, such as aluminum. In certain embodiments, heat spreader 15 transfers heat to a sold body, and in other embodiments heat spreader 15 transfers heat to a fluid. In certain embodiments heat spreader 15 may be a cold plate, heat sink, or other equivalent cooling apparatus.

Heat spreader 15 includes one or more sensors 10. Sensor 10 measures surface flatness and may be located on an external or internal surface of heat spreader 15. In some embodiments, sensor 10 is located on the bottom surface of heat spreader 15. In other embodiments, sensor 10 is located on an opposite internal surface of the bottom heat spreader 15. By measuring surface flatness, sensor 10 may determine whether heat spreader 15 is flat against another surface. When multiple sensors 10 are utilized, it may be determined whether heat spreader 15 is flat against another surface in multiple locations. In certain embodiments sensor 10 may be an electric strain gauge (e.g., electric resistance wire strain gage, etc.). The surface flatness measurement methods utilized by sensor 10 to determine whether heat spreader 15 is flat against another surface are described further herein.

Figure 2:
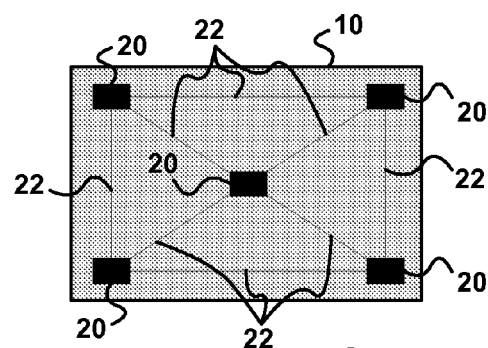
FIG. 2 depicts a sensor according to an embodiment of the present invention.

FIG. 2 depicts a sensor 10 according to various embodiments of the present invention. Sensor 10 includes a plurality of nodes 20 interconnected by connections 22. Though FIG. 2 depicts five nodes 20, alternative numbers of nodes 20 may be utilized in sensor 10. For example, in certain embodiments two nodes 20 are included in sensor 10. In certain embodiments, a first node 20 is connected to a second node 20 by an electric conductive connection 22. In certain embodiments connection 22 may be a wire or any other equivalent electric conductor. In certain embodiments connection 22 is composed of an electric conductor with an electric resistivity, length, and cross-sectional area. The resistance of connection 22 therefore becomes a function of connection 22 geometry, whereby connection 22 resistance changes if connection 22 geometry changes. Consequently, connection 22 resistance increases with increasing strain (e.g., a increasing length, decreasing cross sectional area, etc.) and decreases with decreasing strain (e.g., a decreasing length, increasing cross sectional area, etc.).

In certain embodiments at least three nodes 20 are included in sensor 10 and are connected by two connections 22. For example, the first node 20 and the second node 20 are connected by a first connection 22 and the second node 20 and the third node 20 are connected by a second connection 22. The first connection 22 and the second connection 22 may have similar resistance properties (i.e., the rate that the first resistance changes is similar to the rate that the second resistance changes). In certain embodiments, the first resistance and the second resistance may be compared to determine whether the resistances are similar. In certain embodiments described further herein, sensor 10 is flat if the first resistance is similar to the second resistance. In other embodiments, the first resistance and/or the second resistance may be compared to a known or predetermined resistance to determine whether sensor 10 is flat.

Figure 3:
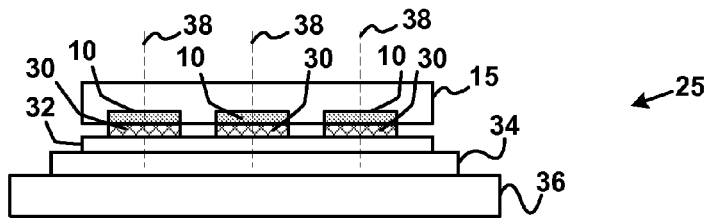
FIG. 3 depicts a heat spreader upon a chip stack according to an embodiment of the present invention.

FIG. 3 depicts a side view of heat spreader 15 upon a chip stack 25 according to various embodiments of the present invention. Chip stack 25 is an electronic package including multiple chips 30 and a substrate 32. In certain embodiments, chip 30 may be an integrated circuit package, semiconductor package, or another component or system, whereby multiple chips 30 may be packaged together upon a shared substrate 32. In another embodiment, chip stack 25 may optionally include an interconnection layer 34 that connects the chip stack 25 to a circuit board 36. Interconnection layer 34 may be for example a grid array (e.g., pin grid array, ball grid array, land grid array, etc.) or other equivalent circuit board interfacing apparatus.

Electronic packing that utilizes multiple chips 30 are gaining in popularity. Further, more and more chips 30 are being packaged into decreasing foot print areas. In certain embodiments, to ensure that heat spreader 15 is in thermal contact with each chip 30, the bottom surface of heat spreader 15 is designed to deform. For example, the bottom surface of heat spreader 15 deforms around a first chip 30 that is slightly higher than a second chip 30 when heat spreader 15 is loaded upon chip stack 25. The deformation allows for the heat spreader 15 to thermally contact both the first chip 30 and the second chip 30 even with the chip 30 height differences.

During device manufacturing a heat spreader 15 is installed and loaded upon chip stack 25. Heat spreader 15 surface flatness changes as the surface of heat spreader 15 deforms. Therefore, one or more sensors 10 may be utilized to measure the flatness of one or more locations of the heat spreader 15 surface. Consequently, in certain embodiments, sensors 10 may be utilized to ensure that heat spreader 15 surface deformations are flat at chip 30 locations. In these embodiments, sensors 10 are placed to oppose chips 30 when heat spreader 15 is loaded upon chip stack 25. For example, axis 38 may bisect both sensor 10 and chip 30.

Figure 4:
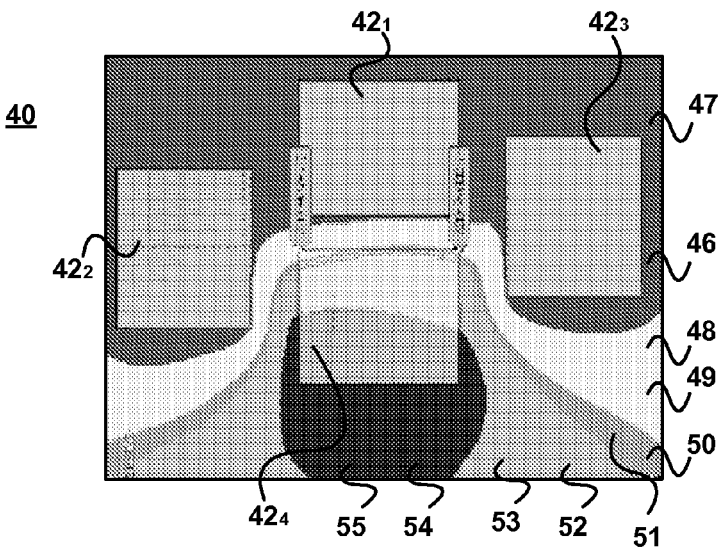
FIG. 4 depicts a gradient map relating to various embodiments of the present invention.

FIG. 4 depicts a gradient map 40 according to various embodiments of the present invention. In alternative embodiments, gradient map 40 may depict gradients of heat transfer between chips 30 and heat spreader 15 or gradients of deformation of heat spreader 15.

For example, gradient map 40 may depict heat transfer gradients between heat spreader 15 and chips 30 of differing heights upon placement of heat spreader 15 upon chip stack 25 but prior to loading heat spreader 15 to chip stack 25 according to an embodiment of the present invention. Gradient map 40 may show a surface of heat spreader 15 and various locations 42. Locations 42 correspond to chips 30. Locations $42_1$, $42_2$, and $42_3$ correspond to chips 30 of the same height and location $42_4$ corresponds to a chip 30 of a differing height (i.e., lower than the other chips). Therefore, when heat spreader 15 is placed upon chip stack 25, heat spreader 15 makes thermal contact with chips 30 at locations $42_1$, $42_2$, and $42_3$ and heat spreader 15 makes minimal (or no) thermal contact with chip 30 corresponding with location $42_4$. In the present example, gradient map 40 may also depict heat transfer gradient areas 46, 48, 50, 52, and 54. A highest level of heat transfer occurs at heat area 46, a high level of heat transfer occurs at heat area 48, a middle level of heat transfer occurs at heat area 50, a low level of heat transfer occurs at heat area 52, and a lowest level of heat transfer occurs at heat area 54. To eliminate the heat transfer gradients and to ensure adequate thermal contact between heat spreader 15 and all chips 30, heat spreader 15 may need to be loaded upon chip stack 25.

In another example, gradient map 40 may depict deformation gradients between heat spreader 15 and chips 30 of differing heights after heat spreader 15 has been loaded upon chip stack 25 according to an embodiment of the present invention. Gradient map 40 may show a surface of heat spreader 15 and various locations 42. Locations 42 correspond to chips 30. Locations $42_1$, $42_2$, and $42_3$ correspond to chips 30 of the same height. Location $42_4$ corresponds to a chip 30 that is offset from the other chips 30. For example, chip 30 corresponding with location $42_4$ is lower than the other chips 30 by 50 mils. In the present example, gradient map 40 may also depict deformation gradient areas 47, 49, 51, 53, and 55. Upon loading, heat spreader 15 may deform thus ensuring adequate thermal contact between heat spreader 15 and chips 30. In the present embodiment, heat spreader 15 deforms a highest amount at deformation area 47 (i.e., high deformation around the relatively higher chips 30), a high amount at deformation area 49, a middle amount at deformation area 51, a low amount at deformation area 53, and a lowest amount at deformation area 55 (i.e., low deformation around the relatively lower chips 30).

Figure 5:
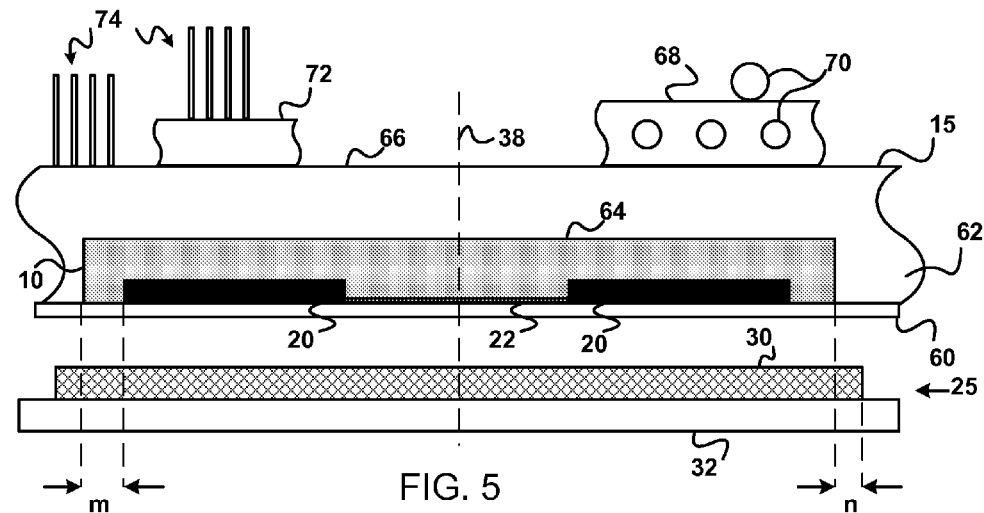
FIG. 5 depicts a heat spreader near a chip according to various embodiments of the present invention.

FIG. 5 depicts a section view of heat spreader 15 near a portion of chip stack 25 according to various embodiments of the present invention. In certain embodiments, heat spreader 15 includes a top portion 62 and bottom portion 60. Bottom portion 60 is a thin wall thermally conductive material and may be relatively compliant compared to top portion 62. Therefore, bottom portion 60 may deform when heat spreader 15 is loaded upon chip stack 25. By deforming, the bottom portion 60 ensures that heat spreader 15 is thermally contacting chip 30 thereby allowing for effective heat transfer between chip 30 and heat spreader 15. For example, after loading heat spreader 15 upon chip stack 25 a minimum threshold amount, wherein some deformation has occurred, and all sensors 10 are indicating flatness, heat spreader 15 may be considered to be in sufficient or adequate thermal contact with chips 30. In certain embodiments, sensor 20 is bonded or is otherwise attached to bottom portion 60 such that sensor 20 may comply with possible bottom portion 60 deformations.

In certain embodiments, heat from chip 30 may be transferred though heat spreader 15 to fins 72, air cooled heat sink 72, or liquid cooled heat sink 68 that are thermally connected to heat spreader 15. Typically fins 72, air cooled heat sink 72, and liquid cooled heat sink 68 are lower in temperature than chip 30 and will thus allow for cooling of chip 30. Air cooled heat sink 72 is a component or assembly that transfers heat generated to a gaseous fluid such as air and is made from a thermally conductive material. In some embodiments, fins 74 may be thermally attached to either air cooled heat sink 72 or to heat spreader 15 to effectively increase the surface area in contact with the surrounding cooling fluid. Liquid cooled heat sink 68 is a component or assembly that transfers heat generated to a liquid fluid such as water. In some embodiments, liquid may flow through one or more passages 70 within liquid cooled heat sink 68. In another embodiment one or more passages 70 may be external to and in thermal contact with liquid cooled heat sink 68 (i.e., passages 70 may be for example a pipe or other liquid carrying apparatus, etc.).

In certain embodiments, dimension 'm' is minimized therefore placing node 20 near the edge of sensor 10. In some embodiments, dimension 'n' is larger than zero to ensure that sensor 10 does not extend from the boundaries of chip 30 where deformation is likely.

Figure 6:
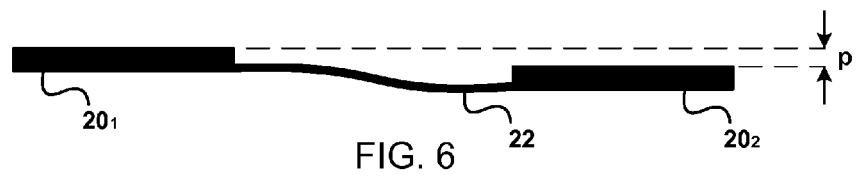
FIG. 6 depicts multiple nodes according to an embodiment of the present invention.

FIG. 6 depicts multiple nodes 20 according to an embodiment of the present invention. A first node $20_1$ is connected to a second node $20_2$ by an electric conductive connection 22. In certain embodiments, connection 22 may be a wire or any other equivalent electric conductor. In certain embodiments, connection 22 is composed of a conductor with a predetermined and known electric resistivity, length, and cross-sectional area. The resistance of connection 22 is a function of connection 22 geometry, whereby connection 22 resistance changes if connection 22 geometry changes. Connection 22 resistance increases with increasing strain (e.g., an increasing length, decreasing cross sectional area, etc.) and decreases with decreasing strain (e.g., a decreasing length, increasing cross sectional area, etc.). Therefore, in certain embodiments a flat connection 22 resistance exists when first node $20_1$ is flat compared to second node $20_2$ (i.e., dimension 'p' is zero, etc.).

First node $20_1$ is higher relative to second node $20_2$ by a dimension 'p'. First node $20_1$ may have become higher during the process of loading heat spreader 15 upon chip stack 25 due to height inconsistencies across chips 30 that may have resulted, for example, from improper or non-ideal assembly of chips 30 upon chip stack 25. Though dimension 'p' is shown relatively large, dimension 'p' is likely to be quite small.

Because first node $20_1$ is higher relative to second node $20_2$ the geometry of connection 22 changes; thus the resistance of connection 22 changes. In certain embodiments, the changing resistance may be compared to the flat connection 22 resistance to determine if first node $20_1$ is flat compared to second node $20_2$.

Figure 7:
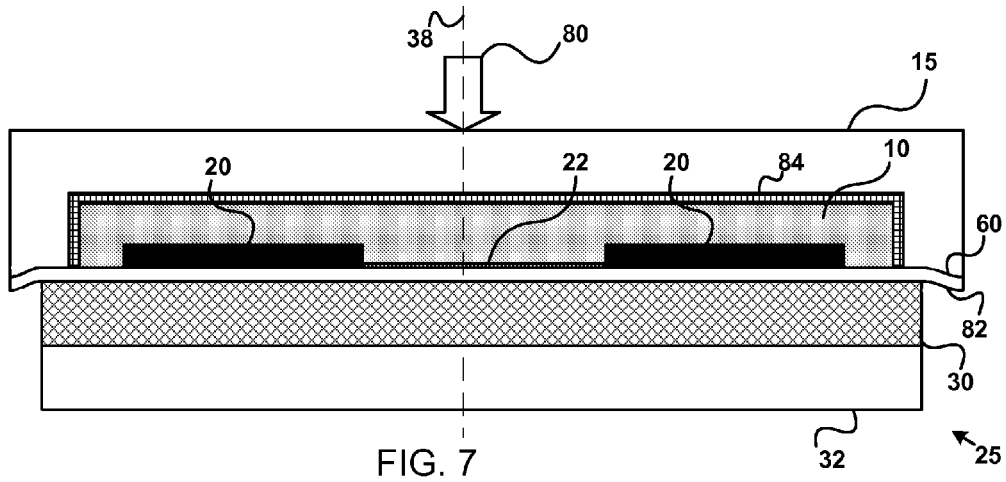
FIG. 7 depicts a heat spreader upon a chip stack according to various embodiments of the present invention.

FIG. 7 depicts a heat spreader 15 upon a chip stack 25 according to various embodiments of the present invention. Heat spreader 15 is loaded upon chip stack 25. In other words, a force 80 is applied to heat spreader 15. Heat spreader 15 deforms around chip 30 to ensure thermal contact between the plurality of chips 30 and heat spreader 15. Therefore, deformations 82 form around chips 30. In certain embodiments, after heat spreader 15 is loaded, a threshold amount and sensors 10 indicate flatness, heat spreader 15 is known to be flat against and in thermal contact with chips 30.

In certain embodiments, a thermal interface material 84 may be utilized to increase heat transfer efficiency. Thermal interface material 84 may be for example a paste or thermal grease, typically silicone oil filled with aluminum oxide, zinc oxide, or boron nitride. Thermal interface material 84 may increase heat transfer efficiency by filling air-gaps that may exist between two surfaces. In another embodiment, a thermal interface material 84 may be utilized as a thermal interface between heat spreader 15 and chip stack 25.

Figure 8:
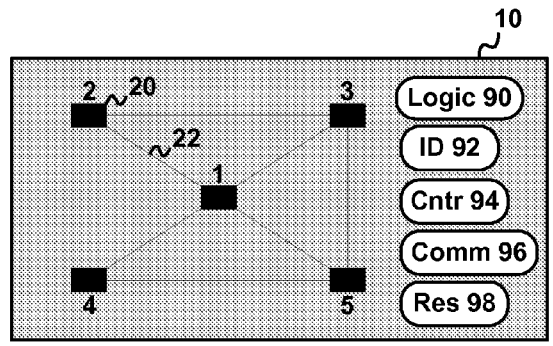
FIG. 8 depicts a sensor according to various embodiments of the present invention.

FIG. 8 depicts a sensor 10 according to various embodiments of the present invention. In certain embodiments, sensor 10 may include a logic engine 90, identification module 92, flat counter 94, communication engine 96, or resistance measurement 98. Logic engine 90 may be utilized to control or manage resistance measurements within sensor 10. Identification module 92 may be utilized, for example, to identify nodes 20 within sensor 10 or to identify the sensor 10 within heat spreader 15. Flat Counter 94 may be utilized to keep a flat count. For example, flat counter 94 may keep a count of the number of connections 22 associated with flat nodes 20 (i.e., dimension 'p' is zero, etc.) or flat counter 94 may keep a count of the number of connections 22 that have similar resistances, etc. Communication engine 96 may be utilized to transfer data, commands, or instructions to or from flatness controller 180 from or to the sensor 10. For example, communication engine 96 may communicate a flat indication to flatness controller 180. Flatness controller 180 is further described below. Resistance measurement 98 may be utilized to measure the resistance of the one or more connections 22. In other embodiments, sensor 10 may also include requisite measurement, data storage/handling, data transmission, hardware, or software apparatuses in order to determine a flatness indication, as is described herein, and to communicate the flatness indication to a higher level electronic structure.

Figure 9:
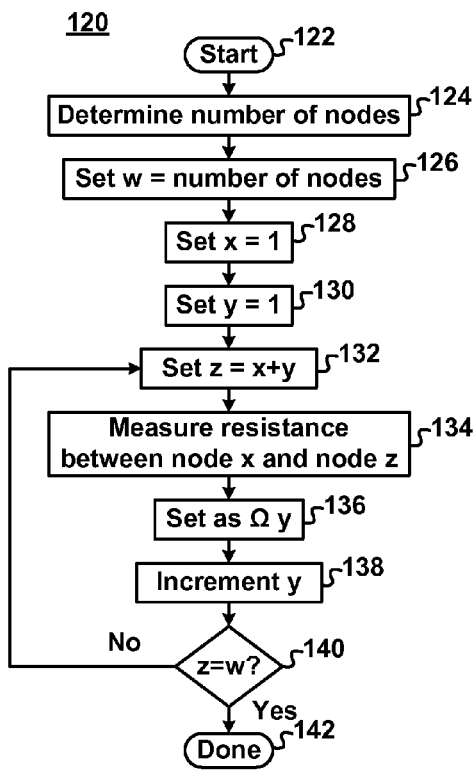
FIG. 9 depicts a measurement method according to various embodiments of the present invention.

FIG. 9 depicts a measurement method 120 according to various embodiments of the present invention. Method 120 may be utilized by sensor 10 to measure resistances of the one or more connections 22. For example, method 120 may be utilized within logic engine 90. Method 120 starts at block 122. The number of nodes 20 within a sensor 10 is determined (block 124). In some embodiments, identification module 92 may accomplish the block 124 determining. A variable 'w' is set to equal the determined number of nodes 20 (block 126). A variable 'x' is set to equal one (block 128). A variable 'y' is set to equal one (block 130). A variable 'z' is set to 'x'+'y' (block 132).

The resistance of connection 22 between node 20 'x' and node 20 'z' is measured (block 134). In other words, the resistance of a connection 22 between a first node 20 and a second node 20 is measured. In some embodiments, resistance measurement 98 may accomplish the block 134 measuring. The measured resistance is set as the variable 'y' resistance (block 138). The variable 'y' is then incremented (block 138). It is determined whether the variable 'z' equals the variable 'w' (block 140). If the variable 'z' does not equal the variable 'w', more resistances need to be measured and method 120 is looped back to block 132. If the variable 'z' equals the variable 'w' all the resistances were measured and method 120 ends at block 142.

In other embodiments, measurement method 120 measures the resistances of the one or more connections 22 and makes those measured resistances available to logic engine 90.

Figure 10:
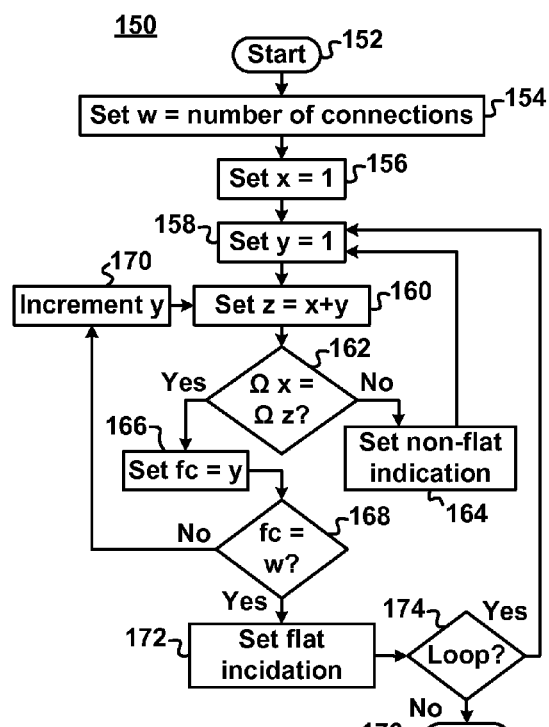
FIG. 10 depicts a measurement comparison method according to various embodiments of the present invention.

FIG. 10 depicts a measurement comparison method 150 according to various embodiments of the present invention. Method 150 may be utilized by sensor 10 to compare the measure resistances of the one or more connections 22. In some embodiments, method 120 may be utilized by logic engine 90. In certain embodiments, method 120 may also be utilized to determine whether nodes 20 are flat relative to each other. Method 150 begins at block 152. A variable 'w' is set equal to the number of connections 22 (block 154). A variable 'x' is set to equal one (block 156). A variable 'y' is set to equal one (block 158). A variable 'z' is set to 'x' +'y' (block 160). Depending upon the embodiment, the values of variables 'w', 'x', 'y', and 'z' in blocks 126, 128, 130, and 132 may or may not equal the values of variables 'w', 'x', 'y', and 'z' in blocks 154, 156, 158, and 160, respectively.

It is determined whether the resistance of the 'x' connection is similar to the resistance of the 'y' connection (block 162). In other words, the resistance of a first connection 22 is compared to the resistance of a second connection 22. If both connections 22 have similar resistance properties, the nodes 20 that are attached to the connections 22 are relatively flat. If the resistance of the 'x' connection is similar to the resistance of the 'y' connection, a flat count is set to equal 'y' (block 166). In some embodiments, the flat count may be kept by flat counter 94. If the resistance of the 'x' connection is not similar to the resistance of the 'y' connection, a non-flat indication is set (block 164). In some embodiments, the non-flat indication may be communicated to flatness controller 180 to indicate that sensor 10 is not flat.

It may be determined if the flat count is similar to the number of connections 22 (block 168). If the flat count is similar to the number of connections 22, the nodes attached to the connections 22 are relatively flat and a flat indication is set (block 172). In some embodiments, the flat indication may be communicated to flatness controller 180 to indicate that sensor 10 is flat. In some embodiments, method 150 may be a continuous method wherein the resistances of connections 22 are repeatedly compared to ensure flatness. Therefore, at block 174, it may be determined whether to loop method 150. If so, method 150 returns to block 158 and if not method 150 ends at block 176. Returning to block 168, if the flat count is not similar to the number of connections 22, the variable 'y' is incremented (block 170), and method 150 returns to block 160.

Figure 11:
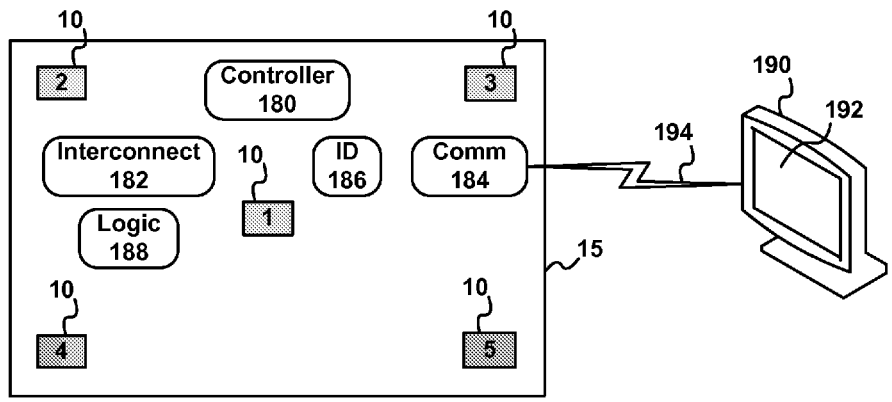
FIG. 11 depicts a heat spreader according to various embodiment of the present invention.

FIG. 11 depicts various embodiments of the present invention in which a display 192 is connected to a heat spreader 15 that may also include a flatness controller 180, interconnects 182, a communication engine 184, identification module 186, or control logic 188. Flatness controller 180 manages or controls flat or non-flat indications received from the one or more sensors 10. Flatness controller 180 may also manage or control flat or non-flat indications sent to a graphics processor, graphic user interface (GUI) 192, etc., associated with display 192. In some embodiments, flatness controller 180 may be a discrete electronic component attached to heat spreader 15 and in other embodiments flatness controller 180 may be a hardware component (e.g., chip 30, etc.) or software component embodied in an electronic component(s) within chip stack 25.

Interconnects 182 are one or more interconnections between the one or more sensors 10 and flatness controller 180. Interconnects 182 are the paths for transfer of data. Examples of such paths are copper wires, optical fibres, wireless communication channels, etc. Communication engine 184 communicates the flat or non-flat indications sent to a graphics processor, graphic user interface (GUI) 192, etc. associated with display 192. In some embodiments, communication engine 184 is connected to, is associated with, or takes the place of communication engine 96. Identification module 186 may identify instances of sensor 10. For example, identification module 186 is able to identify from which sensor 10 a flatness indication is associated with. Control logic 188 is utilized to manage the determination of whether the one or more sensors 10 are flat and may be further utilized to determine when to send flatness indications to display 192 components.

In various embodiments, interconnects 182, communication engine 184, identification module 186, or control logic 188 maybe, for example, sub components of or embodied within flatness controller 180.

In another embodiment heat spreader 15 is connected via connection 194 to a display 190. Display 190 may be utilized by a user during manufacturing when loading heat spreader 15 to chip stack 25. Display 190 may include a GUI 192 that at least depicts an indication when heat spreader 15 is flat. GUI 192 may also give an indication when particular locations of heat spreader 15 (corresponding with sensor 10 locations, etc.) are flat. In other embodiments GUI 192 may also depict when heat spreader 15 is not flat. The flat or non-flat indication associated with GUI 192 may be used by the user may to adjust the loading of heat spreader 15 upon chip stack 25. For example, if the user is notified of a flat indication by GUI 192, the user could terminate the loading of heat spreader 15.

In various embodiments display 190 includes graphics processing hardware and software components in order to display a flat or non-flat indication associated with various location(s) of heat spreader 15 as indicated by, for example, flatness controller 180.

Connection 194 is one or more interconnections between the heat spreader 15 and display 190. Connection 194 is a path for transfer of data and maybe, for example, a copper wire, optical fibre, wireless communication channels, etc. In some embodiments connection 194 may be connected to communication engine 184, controller 180, etc. In some embodiments, connection 194 is a direct path from heat spreader 15 to display 64. In other embodiments, connection 194 may be a path from heat spreader 15 through processing (i.e., chip 30, etc.) and input/output channels of an electronic device to display 190.

Figure 12:
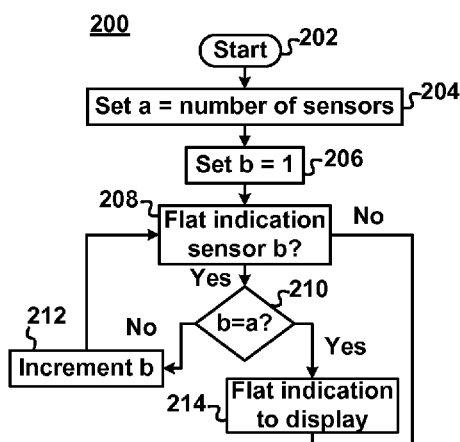
FIG. 12-FIG. 14 depict communication management methods according to various embodiments of the present invention.

FIG. 12 depicts communication management method 200 according to various embodiments of the present invention. Method 200 may be utilized by heat spreader 15 to determine when to send a flat indication that may ultimately be displayed on display 190. For example, method 200 may be utilized within control logic 188 and/or when it is desired that a flat indication be sent to display 90 when all of the sensors 10 within heat spreader 15 have or are showing a flat indication.

Method 200 starts at block 202. A variable 'a' is set to equal the number of sensors 10 (block 204) and a variable 'b' is set equal to one (block 206). It is determined whether sensor 'b' has or is indicating a flat indication (block 208). If sensor 'b' has or is indicating a flat indication, it is determined whether the variable 'b' is similar to the variable 'a' or the number of sensors 10 (block 210). If sensor 'b' has not or is not indicating a flat indication, method 200 ends at block 216.

Returning to block 210, if the variable 'b' is similar to the variable 'a', a flat indication is sent to display 190 (block 214) and method 200 ends at block 216. If the variable 'b' is not similar to the variable 'a', the variable 'b' is incremented (block 212) and method 200 is returned to block 208.

Figure 13:
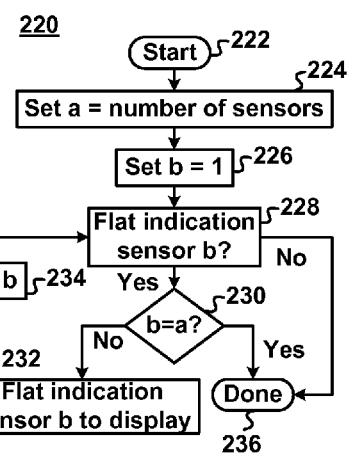

FIG. 13 depicts communication management method 220 according to various embodiments of the present invention. Method 220 may be utilized by heat spreader 15 to determine when to send a flat indication that may ultimately be displayed on display 190. For example, method 220 may be utilized within control logic 188 and/or when it is desired that individual sensor 10 location based flat indications be sent to display 90.

Method 220 begins at block 222. A variable 'a' is set to equal the number of sensors 10 (block 224) and a variable 'b' is set equal to one (block 226). It is determined whether sensor 'b' has or is indicating a flat indication (block 228). If sensor 'b' has or is indicating a flat indication, it is determined whether the variable 'b' is similar to the variable 'a' or the number of sensors 10 (block 230). If sensor 'b' has not or is not indicating a flat indication, method 200 ends at block 236.

Returning to block 230, if the variable 'b' is similar to the variable 'a', method 220 ends at block 236. If the variable 'b' is not similar to the variable 'a', a flat indication corresponding to sensor 10 'b' is sent to display 190 (block 232). The variable 'b' is incremented (block 234) and method 220 returns to block 228.

Figure 14:
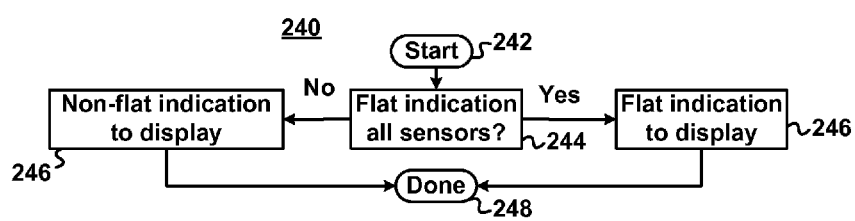

FIG. 14 depicts communication management method 240 according to various embodiments of the present invention. Method 240 may be utilized by heat spreader 15 to determine when to send a flat indication that may ultimately be displayed on display 190. For example, method 240 may be utilized within control logic 188 and/or when it is desired that a flat indication be sent to display 90 when all of the sensors 10 within heat spreader 15 have or are showing a flat indication.

Method 240 begins at block 242. It is determined whether all the sensors 10 within the heat spreader 15 are showing a flat indication (block 244). If all the sensors 10 within the heat spreader 15 are showing a flat indication, a flat indication is sent to display 190 (block 246). If all the sensors 10 within the heat spreader 15 are not showing a flat indication, a non-flat indication is sent to display 190 (block 246).

Figure 15:
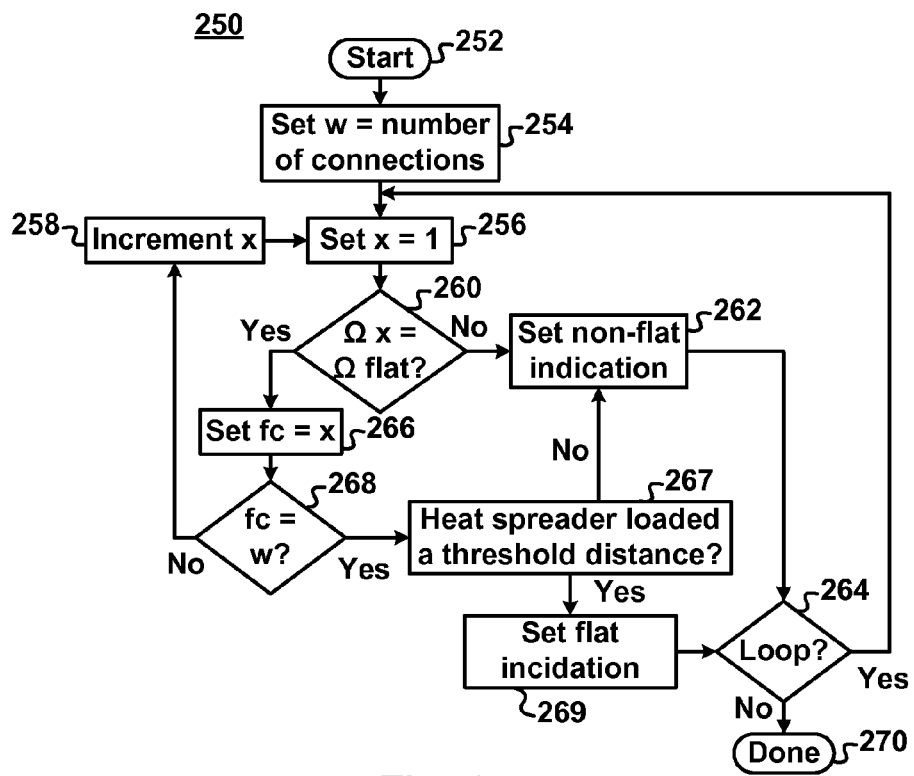
FIG. 15 depicts an alternative measurement comparison method according to various embodiments of the present invention.

FIG. 15 depicts an alternative measurement method 250 according to various embodiments of the present invention. Method 250 may be utilized by sensor 10 to determine whether to set a flat indication or a non-flat indication that may ultimately be communicated to flatness controller 180. In certain embodiments method 250 may be utilized within logic engine 90. Method 250 starts at block 252.

A variable 'w' is set to equal the number of connections 22 (block 254) and a variable 'x' is set equal to one (block 256). It is determined whether resistance of connection 'x' is equal to a predetermined flat resistance (block 260). If resistance of connection 'x' is equal to a predetermined flat resistance, the flat count is set equal to 'x' (block 266). If resistance of connection 'x' is not equal to a predetermined flat resistance, a non-flat indication is set (block 262).

Returning to block 266, it is then determined whether the flat count is equal to variable 'w' (block 268). If the flat count is not equal to variable 'w', the variable 'x' is incremented (block 258) and method 250 returns to block 256. If the flat count is equal to variable 'w', it is determined whether heat spreader 15 has been loaded a threshold amount or distance (block 267). If heat spreader 15 has been loaded a threshold amount or distance, a flat indication is set (block 269). If heat spreader 15 has not been loaded a threshold amount or distance, method 250 returns to block 262.

At block 264, it is determined whether method 250 should loop. If method 250 should not loop, method 250 ends at block 270. If method 250 should loop, method 250 returns to block 256.

The foregoing description of various embodiments of the invention has been presented for the purposes of illustration and description. It is not intended to be exhaustive or to limit the invention to the precise form disclosed. Many modifications and variations are possible in light of the above teaching. It is intended that the scope of the invention be limited not by this detailed description, but rather by the claims appended hereto. Further, since many embodiments of the invention can be made without departing from the spirit and scope of the invention, the invention resides in the claims herein after appended.

The invention claimed is:

1. An electronic device comprising:
a heat spreader comprising at least one sensor that indicates whether the heat spreader is flat against a chip stack.

2. The electronic device of claim 1, wherein the heat spreader further comprises:
a top portion and a bottom portion, the bottom portion configured to deform around the chip stack.

3. The electronic device of claim 1, wherein the sensor further comprises:
a first node and a second node interconnected by a connection having resistivity properties.

4. The electronic device of claim 3, wherein the indication whether the heat spreader is flat against the chip stack is accomplished by at least monitoring changes in the resistivity properties of the connection.

5. The electronic device of claim 1, wherein the chip stack comprises a plurality of chips and wherein the number of the plurality of chips is similar to the number of sensors.

6. The electronic device of claim 1, wherein the location of the sensor corresponds to a location of the chip stack upon the loading of the heat spreader to the chip stack.

7. The electronic device of claim 1, wherein the heat spreader further comprises:
a thermal interface material that thermally connects the sensor to the top portion.

8. The electronic device of claim 1, further comprising:
a display commutatively connected to the heat spreader that visually indicates whether the heat spreader is flat against the chip stack.

9. A method comprising:
indicating whether a heat spreader is flat against a chip stack with a sensor comprised within the heat spreader.

10. The method of claim 9, further comprising:
deforming a bottom portion of the heat spreader around the chip stack.

11. The method of claim 9, further comprising:
measuring, with the sensor, a resistance between a first node and a second node.

12. The method of claim 9, further comprising:
monitoring, with the sensor, resistance changes between a first node and a second node.

13. The method of claim 9, further comprising:
determining whether the sensor is flat based upon a comparison of multiple resistances between a first node and a second node.

14. The method of claim 9, further comprising:
correlating sensor flatness to heat spreader flatness.

15. The method of claim 9, further comprising:
setting a flat count if a comparison of multiple resistances between a first node and a second node indicates resistance similarity.

16. The method of claim 15 further comprising:
setting a sensor flatness indication if the flat count exceeds a threshold.

17. The method of claim 9, further comprising:
indicating non-flatness if a comparison of resistances between a first node and a second node indicates a resistance difference.

18. A computer program product for determining heat spreader flatness, the computer program product comprising:
a computer readable storage medium having computer readable program code embodied therewith, the computer readable program code configured to:
indicate, utilizing a sensor, whether a heat spreader is flat against a chip stack, the sensor comprised within the heat spreader.

19. The computer program product of claim 18 wherein the computer readable program code is further configured to:
measure, utilizing the sensor, a resistance between a first node and a second node.

20. The computer program product of claim 18 wherein the computer readable program code is further configured to:
monitor, with the sensor, resistance changes between a first node and a second node.

* * * * *